United States Patent
Wagener et al.

(10) Patent No.: US 12,180,324 B2
(45) Date of Patent: Dec. 31, 2024

(54) HIGH TEMPERATURE BULK METATHESIS POLYMERIZATION

(71) Applicant: UNIVERSITY OF FLORIDA RESEARCH FOUNDATION, INCORPORATED, Gainesville, FL (US)

(72) Inventors: Kenneth B. Wagener, Gainesville, FL (US); Julia Grace Pribyl, Gainesville, FL (US); Michael H. Bell, North East, MD (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 616 days.

(21) Appl. No.: 17/598,975

(22) PCT Filed: Mar. 30, 2020

(86) PCT No.: PCT/US2020/025739
§ 371 (c)(1),
(2) Date: Sep. 28, 2021

(87) PCT Pub. No.: WO2020/214399
PCT Pub. Date: Oct. 22, 2020

(65) Prior Publication Data
US 2022/0195078 A1   Jun. 23, 2022

Related U.S. Application Data

(60) Provisional application No. 62/825,362, filed on Mar. 28, 2019.

(51) Int. Cl.
*C08F 4/80* (2006.01)
*B01J 31/22* (2006.01)
(Continued)

(52) U.S. Cl.
CPC ............ *C08F 4/80* (2013.01); *C07F 15/0046* (2013.01); *C08F 36/045* (2013.01); *C08F 36/14* (2013.01); *B01J 31/2278* (2013.01)

(58) Field of Classification Search
None
See application file for complete search history.

(56) References Cited

U.S. PATENT DOCUMENTS

2003/0100783 A1   5/2003   Grubbs et al.
2010/0022789 A1   1/2010   Mignani et al.
(Continued)

FOREIGN PATENT DOCUMENTS

WO   20200214399 A2   10/2020

OTHER PUBLICATIONS

PCT/US2020/025739, PCT Search Report & Written Opinion mailed Oct. 9, 2020, 7 pages.

(Continued)

*Primary Examiner* — Richard A. Huhn
(74) *Attorney, Agent, or Firm* — Timothy H. Van Dyke; Wolter Van Dyke Davis, PLLC

(57) ABSTRACT

A method of carrying out a metathesis reaction includes the combination of at least one alkene or non conjugated diene with a Ruthenium-based catalyst with an cyclic(alkyl)(amino)carbene ligand to form a reaction mixture, heating the reaction mixture to a temperature of 100° C. or greater in the absence of a solvent in bulk conditions, and mechanically stirring the reaction mixture. The reaction can be an ADMET, ROMP, a metathesis ring-closure or an olefin exchange reaction.

11 Claims, 7 Drawing Sheets

(51) Int. Cl.
  *C07F 15/00*  (2006.01)
  *C08F 36/04*  (2006.01)
  *C08F 36/14*  (2006.01)

(56) References Cited

U.S. PATENT DOCUMENTS

2018/0265532 A1    9/2018   Giardello et al.
2019/0062493 A1*   2/2019   Wagener ............... C08G 61/08

OTHER PUBLICATIONS

Dinger, Maarten B. et al., "Degradation of the First-Generation Grubbs Methathesis Catalyst with Primary Alchohols, Water, and Oxygen. Formation and Catalytic Activity of Ruthenium (II) Monocarbonyl Species", Organometallics, 2003, vol. 22, pp. 1089-1095.

Fokou, Patrice A. et al., "Studying and Suppressing Olefin Isomerization Side Reactions During ADMET Polymerizations", Macromol. Rapid Commun., 2010, vol. 31, pp. 368-373.

Gaines, Taylor W. et al., "High Melting Precision Sulfone Polyethylens Synthesized by ADMET Chemistry", Macromol. Chem. Phys., 2016, vol. 217, pp. 2351-2359.

Lehman, Stephen E. et al., "Olefin isomerization promoted by olefin metathesis catalysts", Inorganica Chimica Acta, 2003, vol. 345, pp. 190-198.

Marx, Vanessa M. et al., "Cyclic Alkyl Amino Carbene (CAAC) Ruthenium Complexes as Remarkably Active Catalysts for Ethenolysis", Angew. Chem. Int. Ed., 2015, vol. 54, pp. 1919-1923.

Weychardt, Holger et al., "Acyclic Diene Metathesis Polymerization of Divinylarenes and Divinylferrocenes with Grubbs-Type Olefin Metathesis Catalysts", Organometallics, 2008, vol. 27, pp. 1479-1485.

\* cited by examiner

HIGH TEMPERATURE BULK METATHESIS POLYMERIZATION

CROSS-REFERENCE TO RELATED APPLICATION

This application claims the benefit of U.S. Provisional Patent Application No. 62/825,362, filed Mar. 28, 2019, titled HIGH TEMPERATURE BULK METATHESIS POLYMERIZATION, which is incorporated by reference herein in its entirety.

STATEMENT REGARDING FEDERALLY SPONSORED RESEARCH OR DEVELOPMENT

This invention was made with government support under W911NF-13-1-0362 awarded by Army/Army Research Office. The government has certain rights in the invention.

BACKGROUND

Early methods for olefin metathesis or olefin disproportionation were performed using ill-defined metathesis catalyst based on group VI and VII transition metals (W, Mo, and Re). The advent of well-defined Grubb's ruthenium type catalysts introduced stability under ambient conditions and functional group tolerance to metathesis chemistry. Olefin metathesis using Grubbs type ruthenium catalysts are traditionally performed at temperatures ranging from 20 to 60° C. Degradation or olefin migration can be problematic at elevated temperatures. Access to elevated reaction temperatures can potentially enhance metathesis chemistry by unlocking products previously unrealized due to thermodynamic constraints. Metathesis polymerization above the polymer's melting temperature can benefit by allowing the resultant polymer chains to remain unconstrained by crystallization to increase chain diffusion and molecular weight during polymerization.

In the case of metathesis polymerization, acyclic diene metathesis polymerization (ADMET) has been shown to be a useful technique for synthesizing precision functional polyolefin derivatives. The resultant polymers are highly crystalline, exhibiting high melting temperatures. As a result, the polymers are synthesized in solution or solid state. Both techniques limit efficient step growth polymerization, restricting the molecular weight attainable. Additionally, solution polymerization requires the application of vacuum during polymerization. Negative pressure is necessary to remove gaseous ethylene and drive the metathesis equilibrium towards polymerization. Weychardt et al. *Organometallics*, 2008, 27 (7), pp 1479-85 developed a procedure using high boiling point solvents thus light vacuum could be applied. While this method is valuable, solvent purification is required and the use of solvent is cumbersome for scale up and industrial process.

Gaines et al. *Macromol. Chem. Phys.* 2016, 217, 2351-9 demonstrated precision aliphatic polysulfones synthesized via ADMET. The polymers displayed high melting temperature which increased with increasing sulfone content. Both bulk and solution polymerization techniques were ineffective at producing high molecular weight polymer. The high melting temperature of the polymer limited polymer molecular weight using bulk synthesis with Grubb's $1^{st}$ generation catalyst. Raising the polymerization temperature to above the melting temperature ($T_m$) of unsaturated polymer product (about 130° C.) degrades the catalyst. Solution polymerization was performed; however, polymer insolubility limited the polymer's molecular weight.

Hence there remains a need for carrying out bulk metathesis reactions at temperatures in excess of 100° C.

BRIEF SUMMARY

Various embodiments are directed to carrying out the metathesis of an olefin, which is an organic molecule with at least one alkene or at least two non-conjugated ene-groups, using a Ruthenium-based catalyst, such as a Hoveyda-Grubbs type catalyst, comprising an asymmetric N-heterocyclic carbene ligand or a cyclic (alkyl)(amino)carbene ligand (hereinafter, a "Ruthenium-based catalyst") with heating the reaction mixture to a temperature greater than 100° C. The metathesis can be part of a metathesis polymerization where, in the case of a ring-opening metathesis polymerization (ROMP), a cyclic monomer or a combination of cyclic monomers are converted to a polymer with ring-opening or, where in the case of an ADMET polymerization, one or more linear α,ω-dieneyl-monomer are condensed with the loss of a small alkene, with the polymer formed after combining the monomer with a Ruthenium-based catalyst and heating to a temperature greater than 100° C. The metathesis can be a ring-closure reaction where an acyclic non-conjugated diene self-condenses in the presence of a Ruthenium-based catalyst when heated to a temperature above 100° C.

More specifically, various embodiments relate to a method for producing a polymer via metathesis polymerization, the method comprising forming a polymerization mixture, the polymerization mixture comprising a Ruthenium-based catalyst comprising a cyclic(alkyl)(amino) carbene ligand, having the structure:

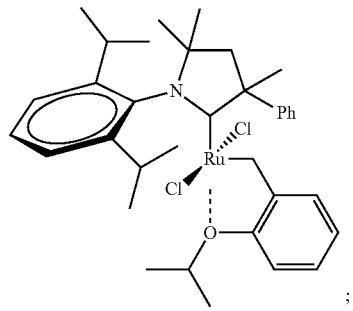

heating the polymerization mixture to a temperature greater than the melting point of the polymer in bulk conditions to form a molten polymerization mixture; and performing intensive mixing on the molten polymerization mixture to produce the polymer. It was unexpectedly discovered that with such a method it is possible for the polymer to have a weight average molecular weight of at least about 10,000 Da within about 3 hours and/or a degree of polymerization of from about 10 to about 100 in from about 3 to about 24 hours.

Variations on the metathesis polymerization and the polymerization mixture are possible. For example, according to various embodiments, the polymerization mixture may further comprise one or more selected from at least one cyclic monomer comprising an alkene, at least one linear monomer comprising an α,ω-dieneyl-monomer, and combinations thereof. According to various embodiments, the at least one cyclic monomer or the at least one linear monomer may comprise a functional group selected from alkyl, aryl, alkylaryl, ketone, aldehyde, ether, ester, carboxylic acid, alkylsilyl, arylsilyl, alkylarylsilyl, amine, epoxy, sulfone, sulfonic acid ester, and amides.

According to various embodiments, the metathesis polymerization may be a metathesis ring-closure, and the polymerization mixture may further comprise at least one acyclic non-conjugated diene. According to various embodiments, the at least one acyclic non-conjugated diene may comprise a functional group selected from alkyl, aryl, alkylaryl, ketone, aldehyde, ether, ester, carboxylic acid, alkylsilyl, arylsilyl, alkylarylsilyl, amine, epoxy, sulfone, sulfonic acid ester, and amides.

According to various embodiments, the metathesis polymerization may be a metathesis olefin exchange, and the polymerization mixture may further comprise at least one alkene. According to various embodiments, the at least one alkene may comprise a functional group selected from alkyl, aryl, alkylaryl, ketone, aldehyde, ether, ester, carboxylic acid, alkylsilyl, arylsilyl, alkylarylsilyl, amine, epoxy, sulfone, sulfonic acid ester, and amides.

According to various embodiments, the melting point of the polymer may be about 100° C. or greater. According to various embodiments, the temperature greater than the melting point of the polymer may be about 120° C. or greater.

According to various embodiments, the polymerization mixture may further comprise a quinone. The quinone may be, for example, benzoquinone.

These and other features, aspects, and advantages of various embodiments will become better understood with reference to the following description, figures, and claims.

BRIEF DESCRIPTION OF THE FIGURES

Many aspects of this disclosure can be better understood with reference to the following figures, in which.

Figure 1:
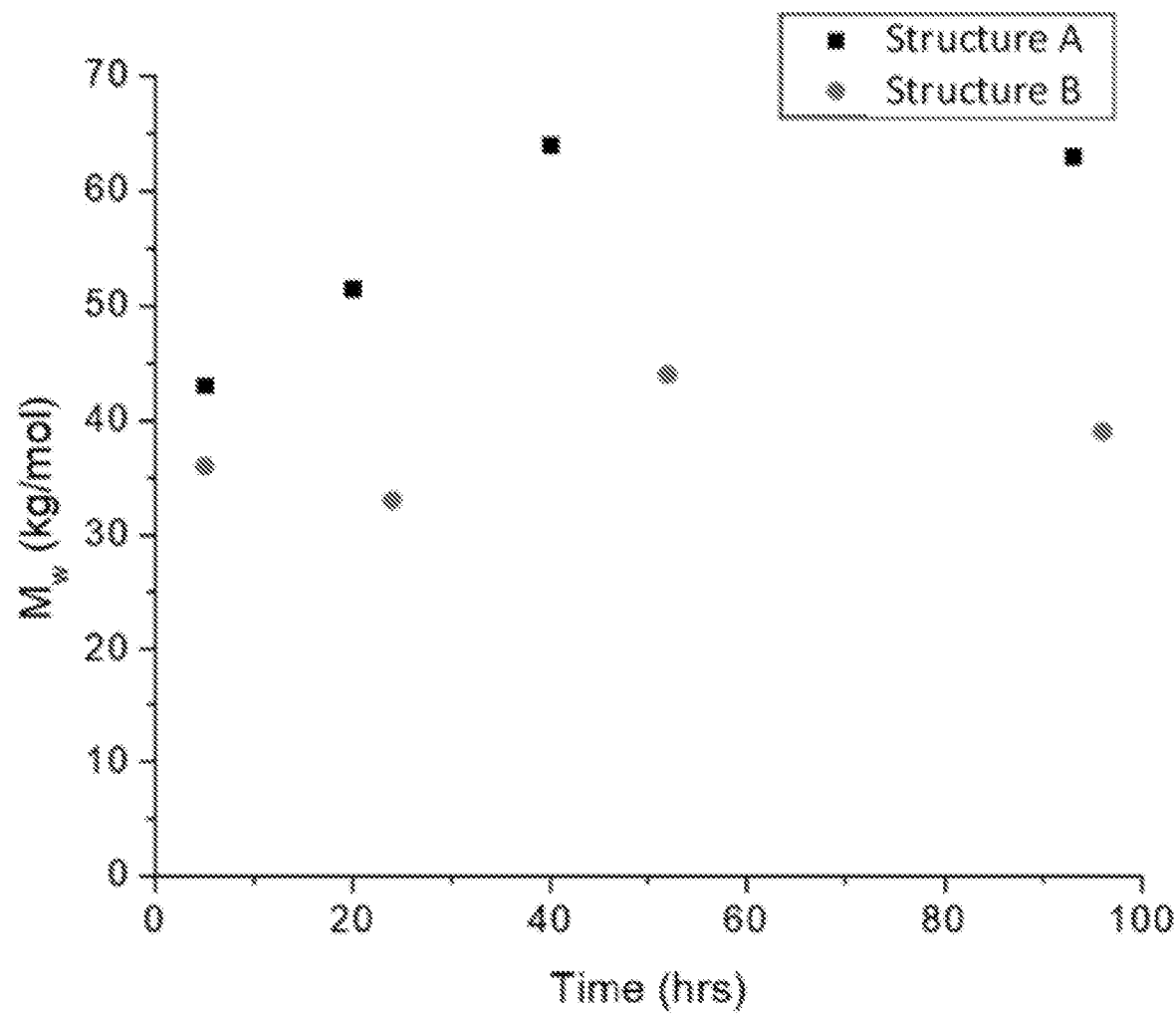
FIG. 1: is an example according to various embodiments, illustrating a plot of weight average molecular weight dependence of unsaturated poly(octylene) on reaction time at 100° C. using a catalyst according to Structure A and a catalyst according to Structure B.

It should be understood that the various embodiments are not limited to the examples illustrated in the figures.

DETAILED DESCRIPTION

Various embodiments may be understood more readily by reference to the following detailed description. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As used herein, the term "bulk" refers to a bulk polymerization carried out in the absence of any solvent or dispersant.

As used herein, the term "standard temperature and pressure" generally refers to 20° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

As used herein, the term "metathesis" generally refers to a reaction involving exchange of substituents between olefins, in other words, transalkylidenation.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Various embodiments are directed to methods of performing metathesis chemistry at temperatures of at least 100° C. and above the melting temperature of the polymer that may employ catalysts in bulk conditions (without solvent). For example, two schematic chemical structures of suitable ruthenium catalysts, are illustrated shown in Structure A and in Structure B.

Structure A

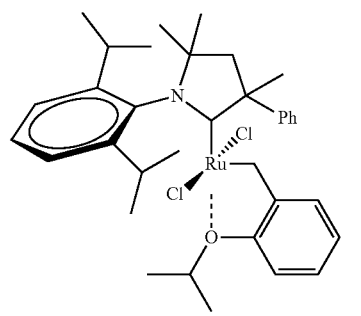

Structure B

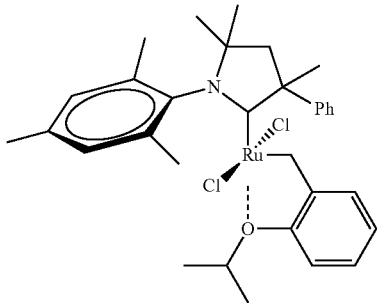

More specifically, Structure A is an example according to various embodiments, illustrating a schematic chemical structure of a ruthenium catalyst that may be used for high temperature metathesis chemistry. Structure B is an example according to various embodiments, illustrating a schematic chemical structure of a ruthenium catalyst that may be used for high temperature metathesis chemistry. The ruthenium catalysts illustrated in Structure A and in Structure B may be referred to as Hoveyda-Grubbs type catalysts that contain asymmetric N-heterocyclic carbene ligands or cyclic(alkyl)(amino) carbene ligands. The catalysts are stable at ambient conditions for extended periods of time.

It has been discovered that other catalysts of similar structure may also be employed, differing in structure to those of Structure A and Structure B by the substitution on the aromatic rings, the alkyl group of the alky aryl ether, and with ligands other than Cl⁻ can be employed as the thermally stable equivalent catalysts for metathesis reactions. For example, Structure C is an example according to various embodiments, illustrating a schematic chemical structure of a ruthenium catalyst that may be used for high temperature metathesis chemistry. Given certain selections of the functional groups ($R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$), Structure C includes or encompasses both Structure A and Structure B.

Structure C

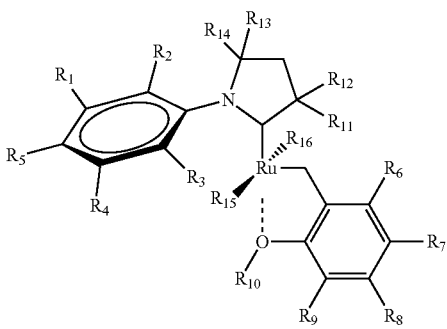

The following lists provide some examples of the functional groups that may be employed in Structure C. The functional groups listed are merely examples; other functional groups may be employed. Referring to Structure C, functional groups $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ may be the same or different and may each be independently selected from hydrogen (H), a linear $C_1$-$C_6$ hydrocarbon, a branched $C_3$-$C_6$ hydrocarbon, and a cyclic $C_3$-$C_6$ hydrocarbon. Still referring to Structure C, functional groups $R_{15}$ and $R_{16}$ may be the same or different and may each be any negative ligand. For example, functional groups $R_{15}$ and $R_{16}$ may be the same or different and may each be independently selected from Cl— (chloro), CN— (cyano), Br— (bromo), O— (oxo), OH— (hydroxo), $CO_3$— (carbonato), $CH_3COO$— (acetato), SCN— (thiocyanato), $SO_4$— (sulphato), $C_2O_4$— (oxalato), and $NO_2$— (nitrito). In this context, "independently selected" means that each group may be chosen from the list of options with out respect to the selection made from the list for any other groups, allowing the functional groups to be the same or different.

Various embodiments are directed to methods of performing metathesis chemistry at temperatures of at least 100° C. in bulk conditions.

Acyclic Diene Metathesis Polymerization (ADMET) Polymerization or Copolymerization According to various embodiments, the high-temperature metathesis polymerization may be an ADMET polymerization or copolymerization, where one or more non-conjugated acyclic diene has a boiling point in excess of 100° C. and a melting point ($T_m$) below the polymerization temperature.

The polymerization temperature may be in a range having a lower limit and/or an upper limit. The range may include or exclude the lower limit and/or the upper limit. The lower limit and/or upper limit can be selected from about 20, 30, 40, 50, 60, 70, 80, 90, 100, 110, 120, 130, 140, 150, 160, 170, 180, 190, and 200° C. For example, according to certain embodiments, the polymerization temperature may be in a range of from about 20° C. to about 200° C., or any combination of lower limits and upper limits described.

The catalyst concentration may be in a range having a lower limit and/or an upper limit. The range may include or exclude the lower limit and/or the upper limit. The lower limit and/or upper limit can be selected from about 0.3, 0.35, 0.4, 0.45, 0.5, 0.55, 0.6, 0.65, 0.7, 0.75, 0.8, 0.85, 0.9, 0.95, and 1 mol percent. For example, according to certain embodiments, the catalyst concentration may be in a range of from about 0.3 to about 1 mol percent, or any combination of lower limits and upper limits described.

The reaction time may be in a range having a lower limit and/or an upper limit. The range may include or exclude the lower limit and/or the upper limit. The lower limit and/or upper limit can be selected from about 0.5, 1, 1.5, 2, 2.5, 3, 3.5, 4, 5, 10, 15, 20, 25, 30, 35, 40, 45, 50, 55, 60, 65, 70, 75, 80, 85, 90, 95, and 100 hrs. For example, according to certain embodiments, the reaction time may be of from about 0.5 to about 100 hrs, or any combination of lower limits and upper limits described.

According to various embodiments, the polymerization or copolymerization may be carried out in the melt in bulk. The polymerization or copolymerization may employ a catalyst as illustrated in Structure A, Structure B, or Structure C, or an equivalent thereof. The polymerization may be carried out at a temperature higher than the melting point of the polymer in the absence of solvent. The acyclic diene may be a functionalized diene or an unfunctionalized diene, where any functionalization does not inhibit or poison the catalyst. If functionalization occurs too close to the terminal olefin (less than 3 methylene spacers) coordination of the functional group with the catalyst could occur simultaneously or preferentially with respect to the olefin. This will limit catalyst/olefin reactivity and therefore polymer molecular weight/reaction progress. A functionalized diene may be functionalized with one or more functional groups. The functional groups may be, separately or in combination, alkyl, aryl, alkylaryl, ketone, aldehyde, ether, ester, carboxylic acid, alkylsilyl, arylsilyl, alkylarylsilyl, amine, epoxy, sulfone, sulfonic acid ester, amides, or any other functional group. Hydrogenation may be performed in any suitable manner.

For example, an unsaturated polymer may be combined with 3 equiv of p-toluenesulfonyl hydrazine (TSH) and tripropylamine (TPA) dissolved in o-xylene or 1,1,2,2-tetrachloroethane. After a bubbler is attached, the reaction mixture may be refluxed until nitrogen is no longer being evolved from the reaction vessel. After addition of more TSH and TPA, the mixture may be refluxed until no more nitrogen is released. The solvent may be removed, and the polymer may be analyzed via 13C and 1H NMR to determine whether complete saturation was achieved According to various other embodiments and examples, hydrogenation has been performed using a 150 mL Parr high-pressure stainless steel reaction vessel equipped with a 50 mL round bottom flask and a Teflon stirring bar/0.15 g of unsaturated polymers may be dissolved in 20 mL of anhydrous toluene and degassed for 1 hour before adding 15 wt % of Pd/C. The round bottom flask was placed into the bomb and then sealed. The Parr vessel was purged with 500 psi of hydrogen gas three times. The bomb was then charged to 900 psi, and the mixture was stirred for 5 days at 90° C. The resultant polymer was filtered and precipitated into cold methanol to obtain a white solid, which was then filtered, transferred to a vial and dried under high vacuum ($3\times10^{-4}$ mmHg) overnight, yielding 0.13 g (87%) of final polymer.

According to various embodiments high-temperature metathesis polymerization may be an ADMET polymerization or copolymerization may produce a polymer or a copolymer having a wide range of molecular weights. The polymers or copolymers may have a weight average (Mw) within a range having a lower limit and/or an upper limit. The range may include or exclude the lower limit and/or the upper limit. The lower limit and/or upper limit can be selected from about 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, and 200 kg/mol. For example, according to certain embodiments, the polymers or copolymers may have a weight average (Mw) of from about 35 to about 130 kg/mol, or any combination of lower limits and upper limits described.

Ring-Opening Metathesis Polymerization (ROMP)

According to various embodiments, the high-temperature metathesis polymerization may be a ring-opening metathesis polymerization (ROMP) or copolymerization carried out at temperatures in excess of 100° C. A functionalized or unfunctionalized cyclic olefin or alkene may have a boiling point in excess of 100° C. and a $T_m$ below the polymerization temperature. Polymerization or copolymerization may optionally be carried out in the melt in bulk. The polymerization or copolymerization may employ a catalyst as illustrated in Structure A, Structure B, or Structure C, or an equivalent thereof.—The polymerization can be carried out to high molecular weights as long as functional groups on the cyclic olefin or alkene does not inhibit or poison the catalyst. The functional groups of the cyclic olefin or alkene may be, separately or in combination, alkyl, aryl, alkylaryl, ketone, aldehyde, ether, ester, carboxylic acid, alkylsilyl, arylsilyl, alkylarylsilyl, amine, epoxy, sulfone, sulfonic acid ester, amides, or any other functional group.

Ring-Closure Metathesis

According to various embodiments, the high-temperature metathesis polymerization may be a ring-closure metathesis can be carried out using the catalysts of Structure A, Structure B, Structure C, or their equivalent. The ring-closure can be carried out at temperatures in excess of 100° C. where a functionalized or unfunctionalized non-conjugated diene has a boiling point in excess of 100° C. and a $T_m$ below the metathesis reaction temperature. The reaction can be carried out in the melt for some dienes and employing a catalyst of Structure A, Structure B, Structure C, or their equivalent. Functional groups of a functionalized non-conjugated diene can be, separately or in combination, alkyl, aryl, alkylaryl, ketone, aldehyde, ether, ester, carboxylic acid, alkylsilyl, arylsilyl, alkylarylsilyl, amine, epoxy, sulfone, sulfonic acid ester, amides, or any other functional group.

Olefin-Exchange Metathesis

According to various embodiments, the high-temperature metathesis chemistry may be olefin-exchange metathesis can be carried out using the catalysts of Structure A, Structure B, Structure C, or their equivalent. The exchange reaction can be carried out at temperatures in excess of 100° C. where a functionalized or unfunctionalized ene, diene, triene or polyene has a boiling point in excess of 100° C. and a $T_m$ below the metathesis reaction temperature. The exchange can be driven to a single product or a plurality of products depending upon the proportion of reactant olefins, their relative concentration, their symmetry, volatility of an exchange product, or other factor. The functional groups can be, separately or in combination, alkyl, aryl, alkylaryl, ketone, aldehyde, ether, ester, carboxylic acid, alkylsilyl, arylsilyl, alkylarylsilyl, amine, epoxy, sulfone, sulfonic acid ester, amides, or any other functional group.

Characteristics of the Resultant Polymers

Methods according to various embodiments produce polymers that lack tacticity, or more formally "stereogenicity". Stereogenicity refers to the presence of chiral centers along the polymer backbone. Chiral centers can only be present when the functional groups are pendant on the polymer backbone. Various embodiments described above produce polymers with the sulfone group incorporated into the polymer backbone. In other words, the sulfone group is not pendant to the polymer backbone and, therefore, by definition, the polymer lacks tacticity or stereogenicity.

Mixing

Different types of mixing may be employed according to various embodiments, which include "extensive mixing" and "intensive mixing." Extensive mixing may also be referred to as blending, mixing and distributive mixing. Intensive mixing may also be referred to as compounding, dispersion, and dispersive mixing. Extensive mixing is essentially stirring together the ingredients and the result is a mixture of ingredients that can in principle, be separated. On the other hand, intensive mixing involves the more intimate dispersion of the additives into the matrix of the polymer. Intensive mixing may require a physical change in the components. For example, a polymer may need to be in the molten or rubbery state during mixing. The mixing is driven by a mechanical motor, and a stirring paddle attached to the motor via a shaft is submerged into the molten reaction mixture. According to various embodiments, the type of mixing that is happening is intensive mixing, in that at the end of the reaction, no monomer is left, only polymer (or oligomers), the additive, and catalyst. The additive and catalyst can in principle be removed from the resulting polymer.

Rate and Degree of Polymerization

The method according to various embodiments, may include heating a polymerization mixture to a temperature greater than the melting point of the polymer, which may be 100° C. or greater, in bulk conditions to form a molten polymerization mixture; and mechanically stirring the molten polymerization mixture. The mechanical stirring may comprising intensive or extensive mixing. According to various embodiments, the polymer has a weight average molecular weight (Mw) of at least about Mw=10,000 Da within about 3 hours. According to various embodiments, a degree of polymerization of from about 10 to about 100 may be achieved in from about 3 to about 24 hours.

EXAMPLES

The following examples are put forth to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. The purpose of the following examples is not to limit the scope of the various embodiments, but merely to provide examples illustrating specific embodiments.

Example 1

A purpose of this example was to illustrate a reaction scheme for high temperature polymerization of bis-pent-4-enesulfone to a poly(oct-4-ene-alt-sulfone) and its hydrogenation to poly(octyl-alt-sulfone). In an exemplary embodiment, the synthesis of poly(octylene) at 100° C. occurs, as shown Reaction Scheme 1, using a catalyst according to Structure A, Structure B, or Structure C. More specifically, Reaction Scheme 1 is an example according to various embodiments, illustrating a reaction scheme for high temperature polymerization of 1,9-decadiene to poly(octylene) and its hydrogenation to polyethylene.

Reaction Scheme 1

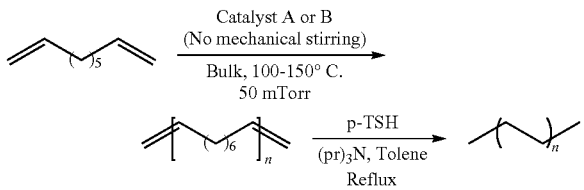

The melting temperature of poly(octylene) is 30° C. by differential scanning calorimetry (DSC). High molecular weight polymer was formed by this step growth polymerization. The poly(octylene) can be converted to polyethylene by hydrogenation, where the melting temperature of the resulting polyethylene is approximately 130° C. The melting temperature indicates that no branching occurs during the polymerization.

FIG. 1 is a plot of weight average molecular weight dependence of unsaturated poly(octylene) on reaction time at 100° C. using a catalyst according to Structure A and a catalyst according to Structure B. Data from FIG. 1 is summarized in Table 1.

TABLE 1

| Catalyst Structure A | | Catalyst Structure B | |
| --- | --- | --- | --- |
| Time (hrs) | Mw (g/mol) | Time (hrs) | Mw (g/mol) |
| 5 | 43000 | 5 | 36000 |
| 20 | 51500 | 24 | 33000 |
| 40 | 64000 | 52 | 44000 |
| 93 | 63000 | 96 | 39000 |

Example 2

A purpose of this example was to illustrate a reaction scheme for high temperature polymerization of bis-pent-4-enesulfone to a poly(oct-4-ene-alt-sulfone) and its hydrogenation to poly(octyl-alt-sulfone).

The synthesis of a sulfone monomer, was carried out as is known in the prior art, for example as disclosed in Gaines et al. Reaction Scheme 2 is an example according to various embodiments, illustrating a reaction scheme for high temperature polymerization of bis-pent-4-enesulfone to a poly(oct-4-ene-alt-sulfone) and its hydrogenation to poly(octyl-alt-sulfone).

Reaction Scheme 2

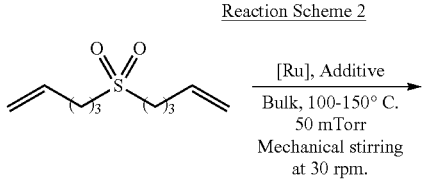

-continued

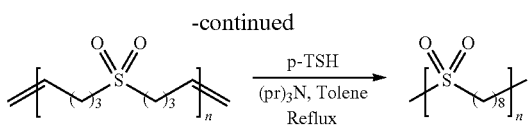

The solid monomer was heated above its melting temperature of 40° C. and degassed. Polymerization was performed at 160° C., for 3 h, at 0.5 mol % catalyst loading in a mechanically stirred reaction vessel with a stirring rate of 30 revolutions per minute (rpm). The mixing may be categorized as intensive mixing.

Figure 2:
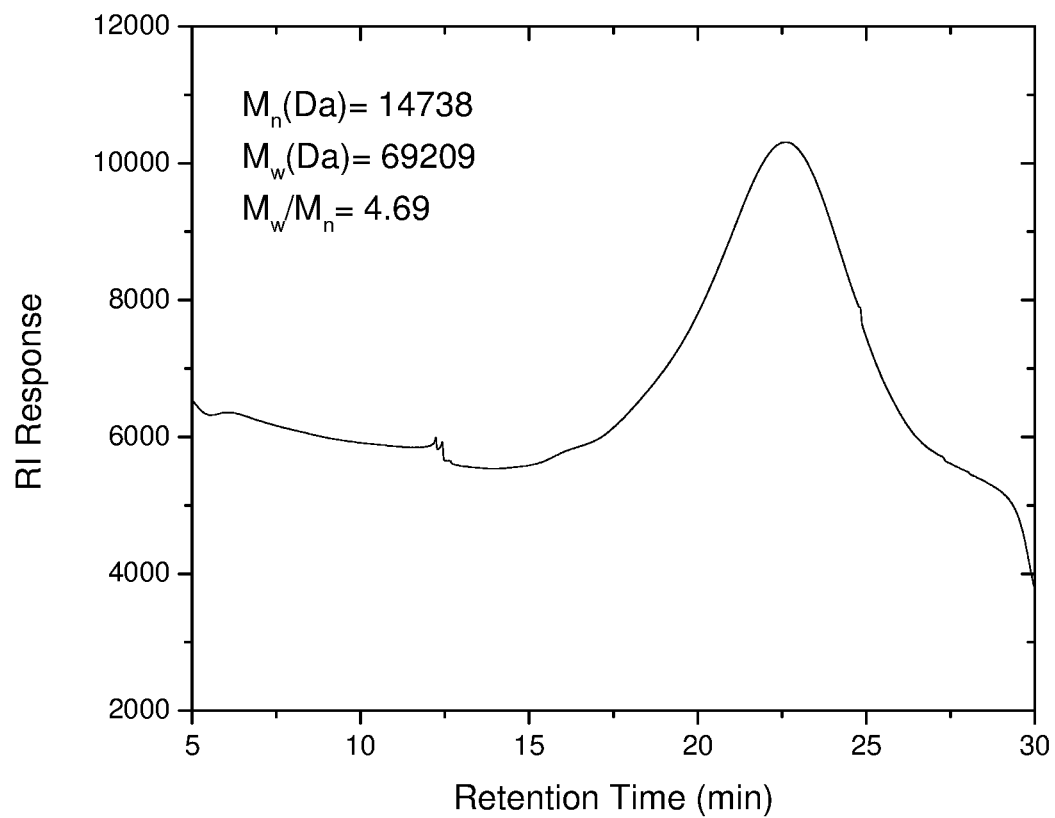
FIG. 2: is an example according to various embodiments, illustrating Gel Permeation Chromatography trace and molecular weight data achieved for poly(oct-4-ene-alt-sulfone) under the bulk conditions, mechanical stirring, and temperature described in Example 2.

FIG. 2 is an example according to various embodiments, illustrating Gel Permeation Chromatography trace and molecular weight data achieved for poly(oct-4-ene-alt-sulfone) under the bulk conditions and temperature described above in a mechanically stirred reactor vessel. Gel permeation chromatography is a size exclusion separation technique in which a polymer solution is flowed through a bed of resin beads. Large polymers elute from the column first, so they are detected at shorter elution times. Smaller polymers take longer to pass through the resin column, so they elute at later times.

Figure 3:
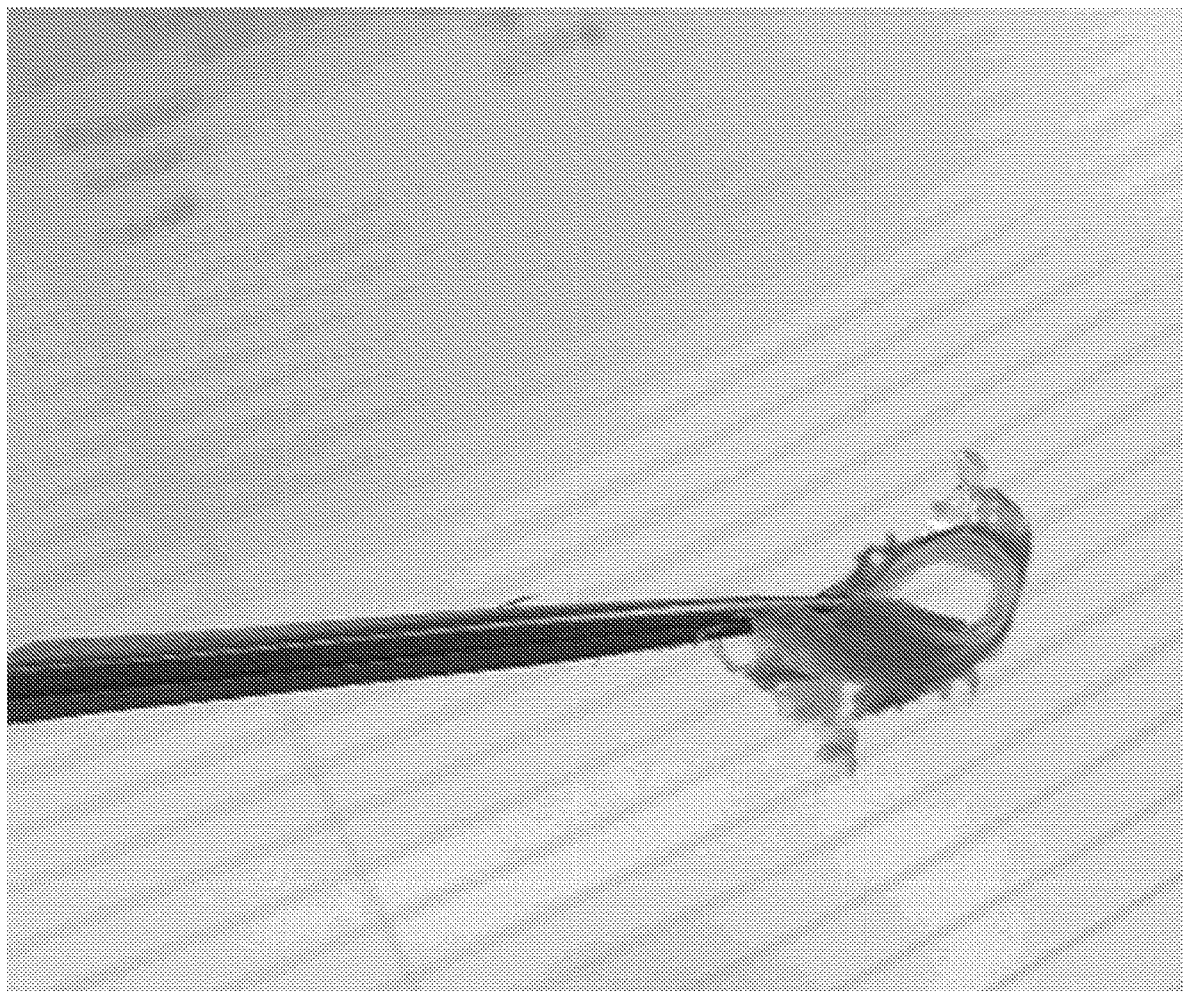
FIG. 3: is an example according to various embodiments, illustrating a photographic image of the flexible poly(oct-4-ene-alt-sulfone) film obtained according to Example 2.
Figure 4:
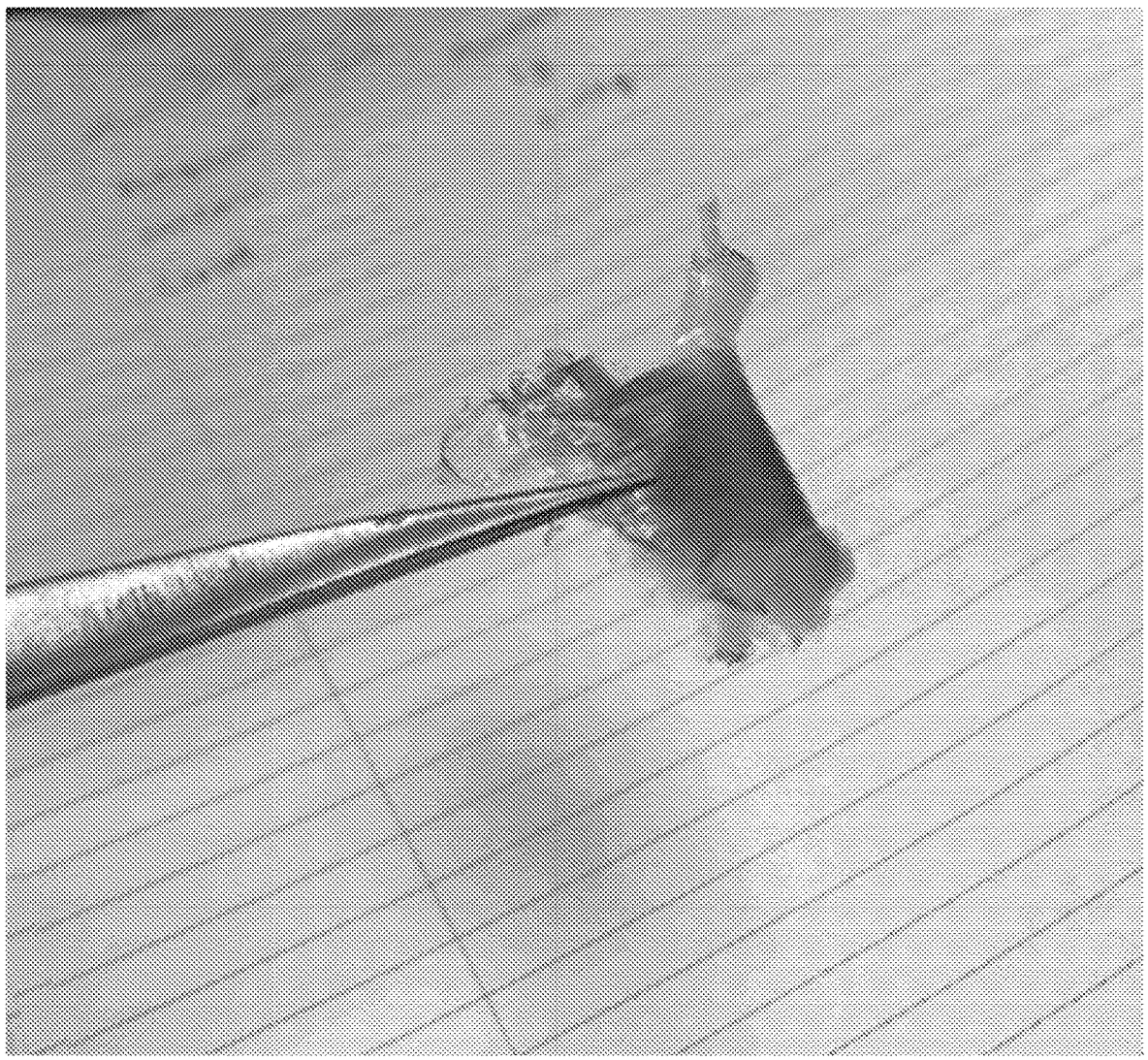
FIG. 4: is an example according to various embodiments, illustrating a photographic image of the flexible poly(oct-4-ene-alt-sulfone) film obtained according to Example 2.

FIG. 3 and FIG. 4 are images of the flexible poly(oct-4-ene-alt-sulfone) film obtained. Film formation indicates that the polymer molecular weight is sufficient for inter-chain entanglement, a result of the mechanical stirring and bulk conditions employed.

Example 3

A purpose of this example was to utilize Differential Scanning calorimetry (DSC) to examine unsaturated poly (oct-4-ene-alt-sulfone) obtained from Example 2 and the same polymer after saturation according to Reaction Scheme 2.

Before saturation, the polymer had a repeating structure according to Structure D. After saturation, the polymer had a repeating structure according to Structure E.

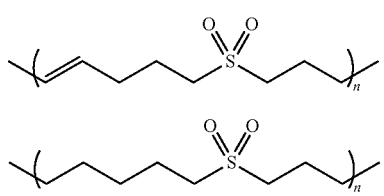

Structure D

Structure E

Both the unsaturated and saturated polymers were subjected to a DSC analysis. DSC is a thermoanalytical technique in which the difference in the amount of heat required to increase the temperature of a sample and reference is measured as a function of temperature. Both the sample and reference are maintained at nearly the same temperature throughout the experiment. The basic principle underlying this technique is that when the sample undergoes a physical transformation such as phase transitions, more or less heat will need to flow to it than the reference to maintain both at the same temperature. The result of a DSC experiment is a curve of heat flux versus temperature or versus time. DSC is used widely for examining polymeric materials to determine their thermal transitions. Important thermal transitions include the glass transition temperature (Tg), crystallization temperature (Tc), and melting temperature (Tm). The observed thermal transitions can be utilized to compare materials, although the transitions alone do not uniquely identify composition.

Figure 5:
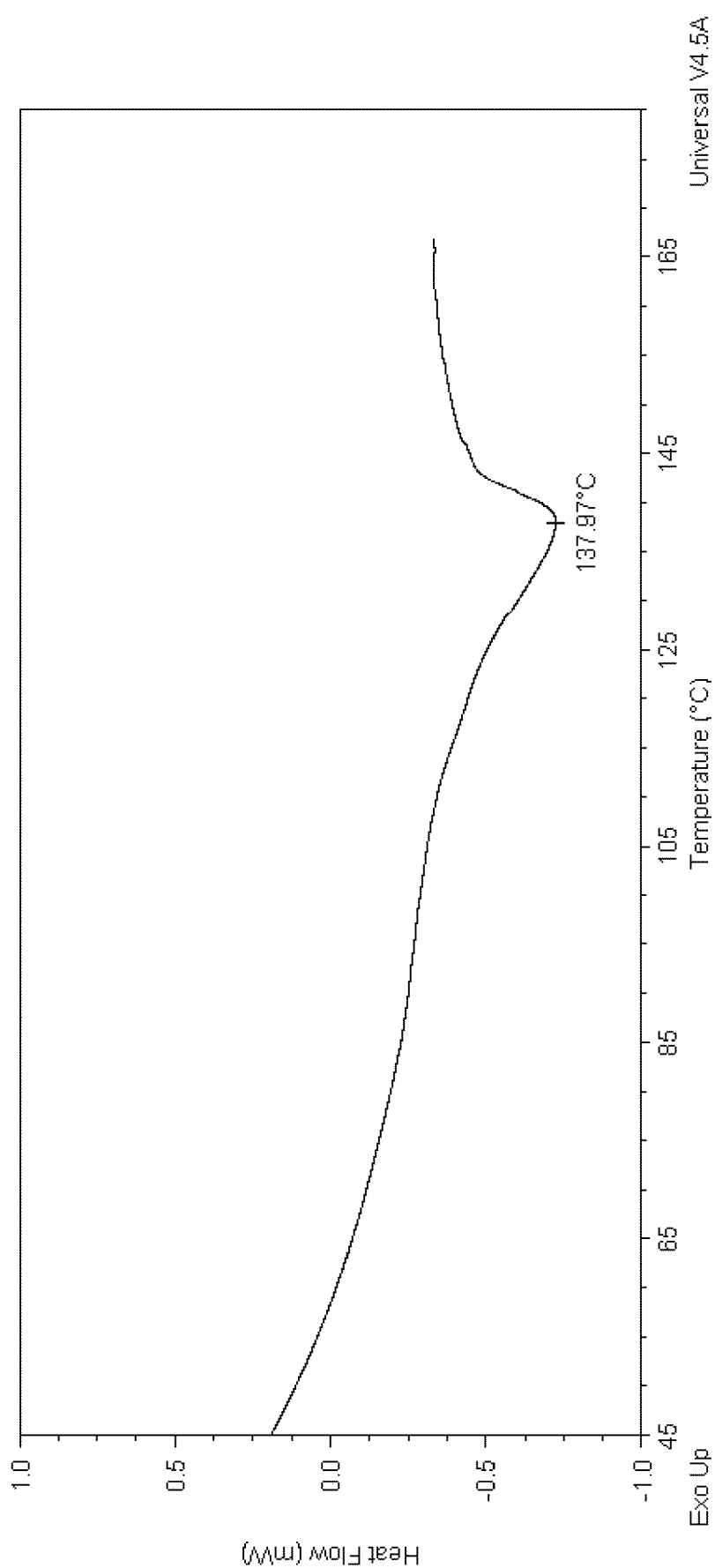
FIG. 5: is an example according to various embodiments, illustrating a DSC plot for the unsaturated poly(oct-4-ene-alt-sulfone) obtained according to Example 2.
Figure 6:
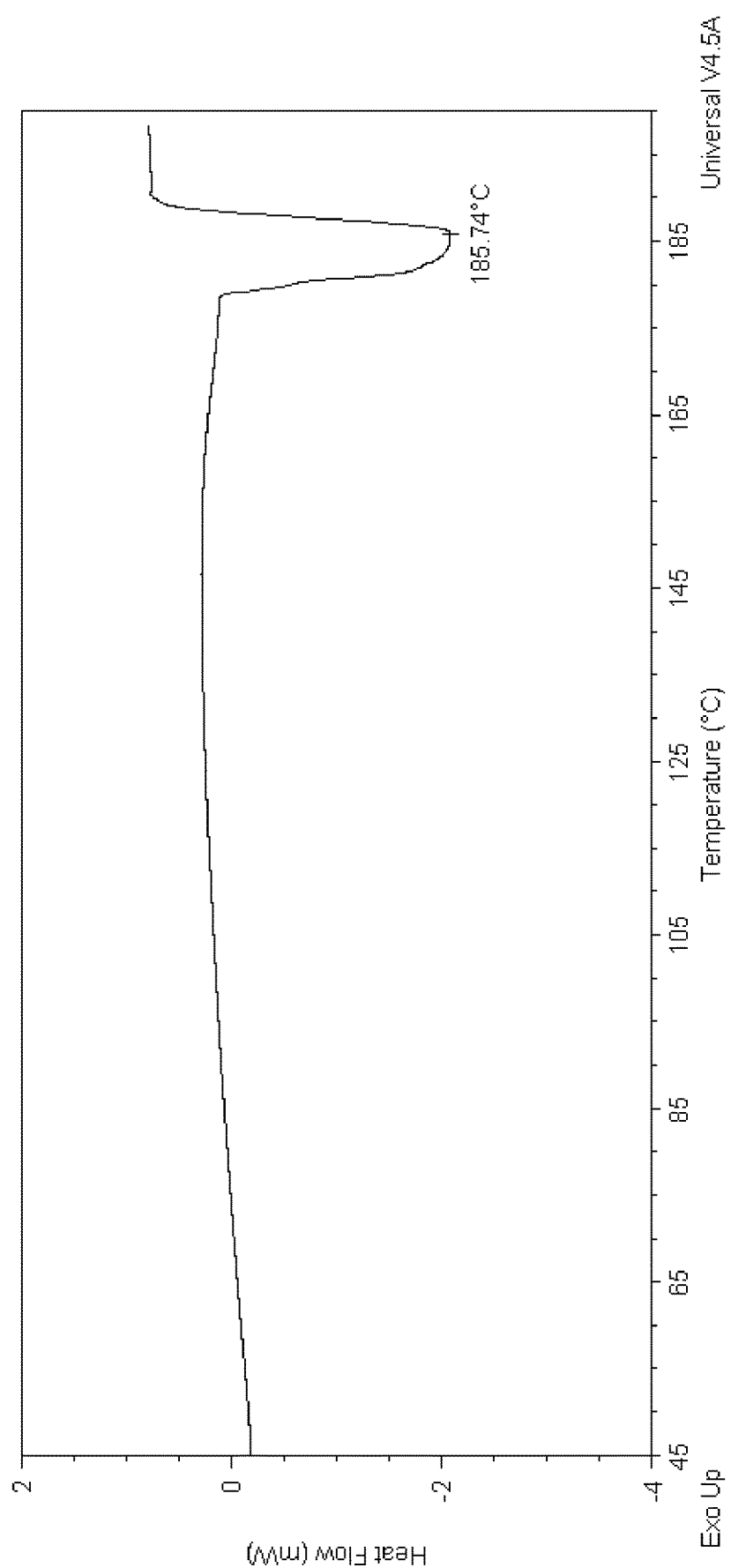
FIG. 6: is an example according to various embodiments, illustrating a DSC plot for the poly(oct-4-ene-alt-sulfone) obtained according to Example 2 after saturation.

FIG. 5 shows a DSC plot for the unsaturated poly(oct-4-ene-alt-sulfone). FIG. 6 shows a DSC plot for the same polymer after saturation. As can be seen by comparing FIG. 5 with FIG. 6, the melting point increase from about 137 degrees Celsius to about 185 degrees Celsius after saturation indicates that the precision placement of sulfone groups is highly conserved. For example, if the melting point did not increase appreciably, that would indicate that the sulfone groups were not spaced regularly throughout the polymer backbone. This lack of regularity would disrupt the polymer crystallization and lead to a low melting point.

Example 4

A purpose of this example was to illustrate a reaction scheme for high temperature polymerization of bis-pent-4-enesulfone to a poly(oct-4-ene-alt-sulfone) and its hydrogenation to poly(octyl-alt-sulfone).

The synthesis of a sulfone monomer, was carried out as is known in the prior art, for example as disclosed in Gaines et al. Reaction Scheme 3 is an example according to various embodiments, illustrating a reaction scheme for high temperature polymerization of bis-pent-4-enesulfone to a poly (oct-4-ene-alt-sulfone) and its hydrogenation to poly(octyl-alt-sulfone).

Reaction Scheme 3

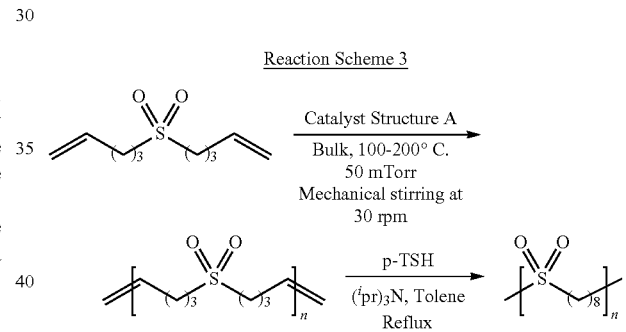

The solid monomer was added to a mechanically stirred reactor vessel and heated above its melting temperature of 40° C. The melted monomer was then cooled to 0° C., then vacuum was applied to remove any evolved gases. This degassing procedure was repeated at least three times to fully remove any dissolved gases present in the monomer. After the last cycle, the monomer was kept at 0° C. while the catalyst was added quickly under inert atmosphere (Argon). Polymerization was then performed at 160° C., with high vacuum applied for 3 h, at 0.5 mol % catalyst loading in a mechanically stirred reaction vessel at a stirring rate of 30 rpm. The mixing may be categorized as intensive mixing.

Figure 7:
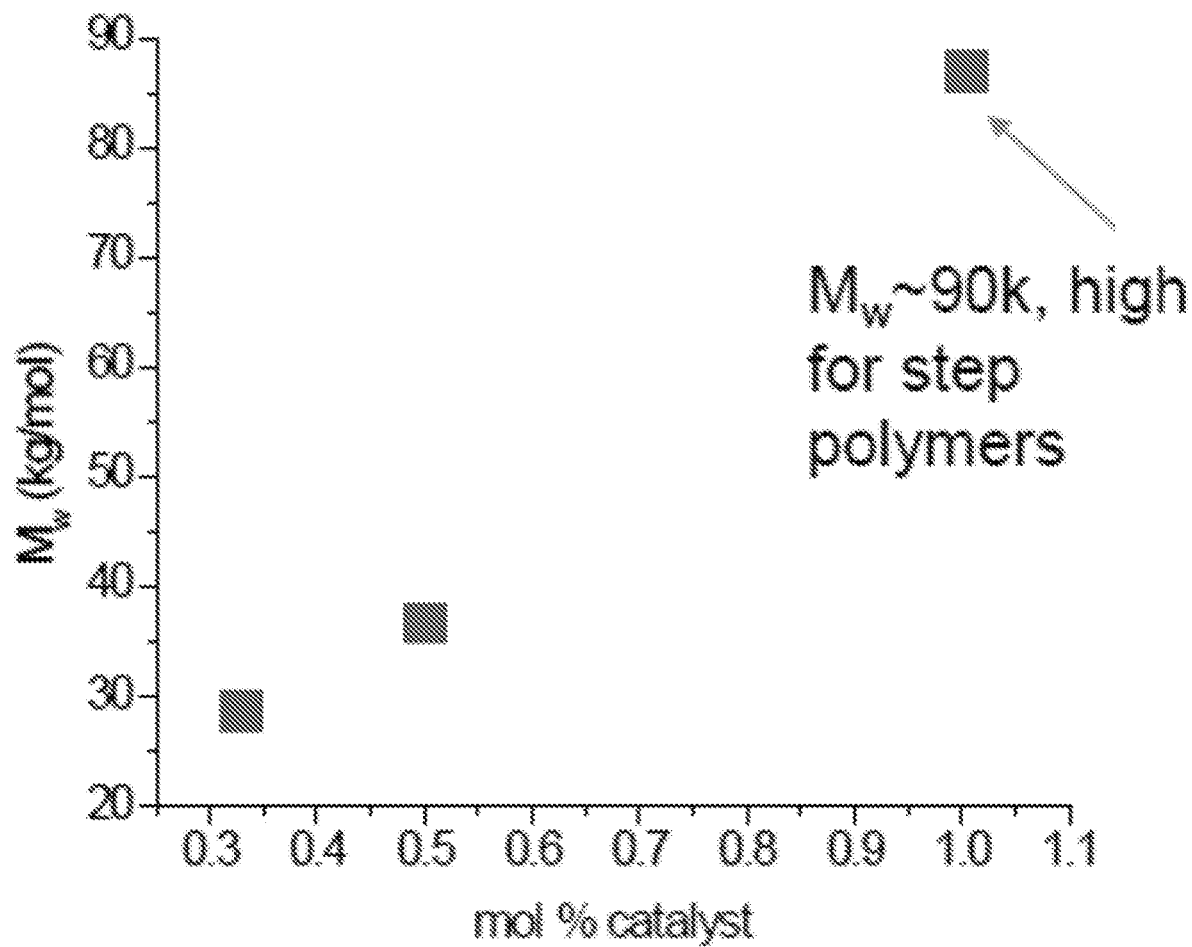
FIG. 7: is an example according to various embodiments, illustrating a plot of the molecular weight of the polymer obtained according to Example 4 for various amounts of catalyst.

FIG. 7 is an example according to various embodiments, illustrating a plot of the molecular weight of the polymer obtained according to Example 4 for various amounts of catalyst. A high molecular weight was obtained.

Example 5

A purpose of this example was to illustrate the results obtained from a 1,2-Olefin Isomerization study. Reaction Scheme 4 is an example according to various embodiments, illustrating the reaction scheme employed. Anthracene methanol (1) was modified with undec-10-enyl bromide to afford structure (2). The cross-metathesis reaction using catalyst structure A was conducted under various conditions outlined in Table 2. The purpose of this study was to observe whether 1,2-olefin metathesis was prevalent under the conditions studied. Based on the general metathesis mechanism, isoform M1 (below) is the predicted structure. If isoforms M2, M3, or M4 were detected by mass spectrometry, that would indicate some degree of 1,2-olefin isomerization was occurring. The results of these mass spectrometry studies are detailed in Table 2. The addition of benzoquinone was found to help lessen 1,2-olefin isomerization.

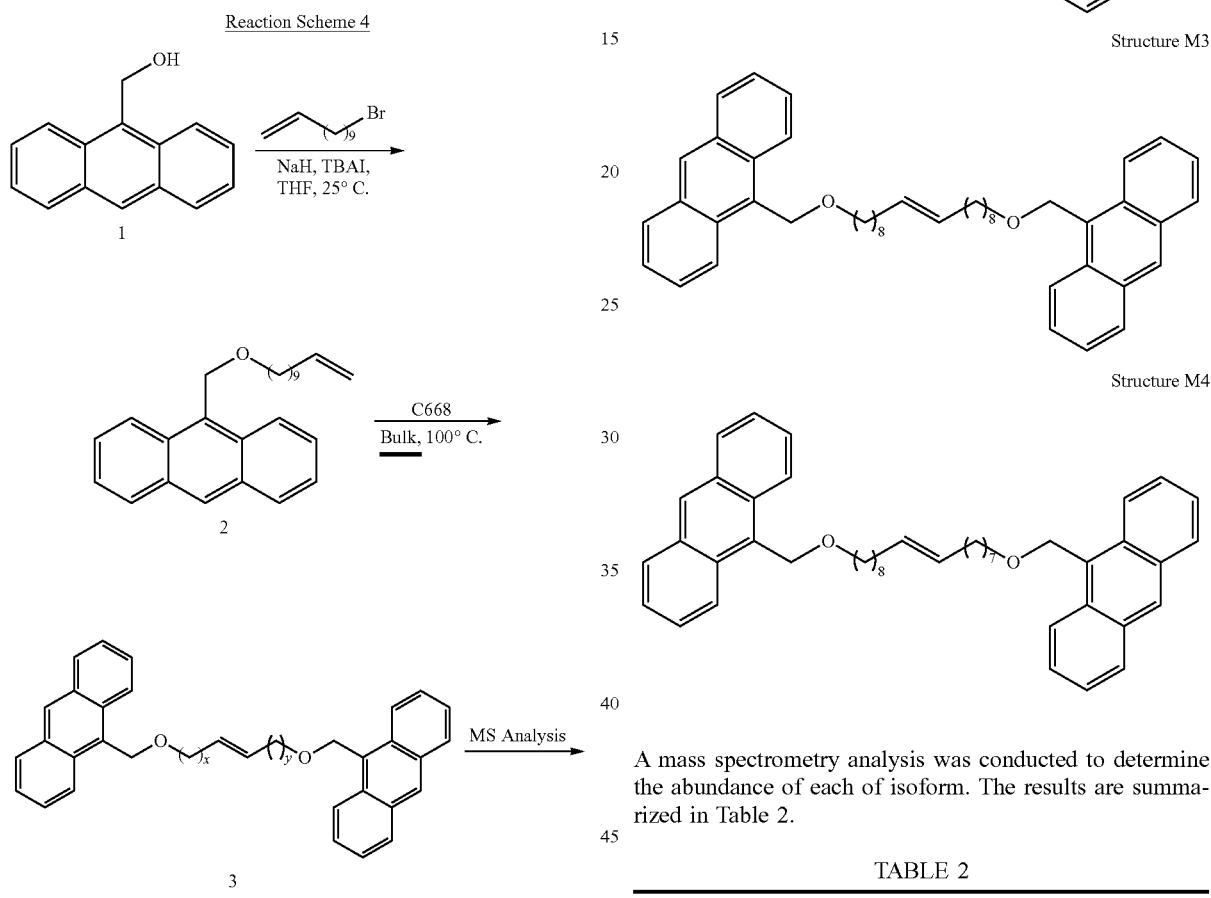

In Reaction Scheme 4, "C668" refers to Catalyst Structure A. Reaction Scheme 4 may result in 4 isoforms, having the structures according to Structure M1, M2, M3, and M4.

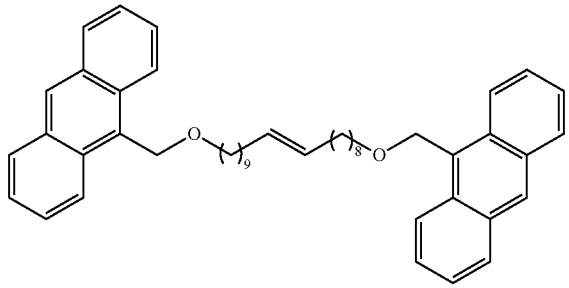

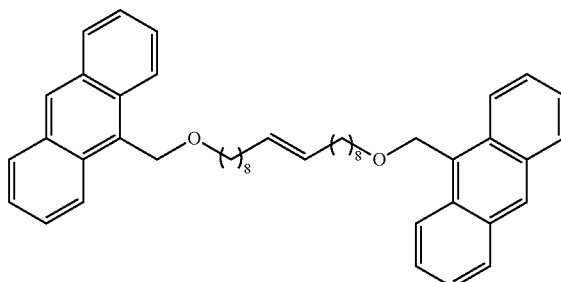

A mass spectrometry analysis was conducted to determine the abundance of each of isoform. The results are summarized in Table 2.

TABLE 2

| | | | Isoform Abundance | | | | |
|---|---|---|---|---|---|---|---|
| Sample | [Catalyst] | Temp ° C. | M1 | M2 | M3 | M4 | % Isomers |
| 1 | 0.5% | 100 | 71 | 23 | 6.0 | 0 | 29 |
| 2 | 1.0% | 100 | 63 | 25 | 8.8 | 2.0 | 37 |
| 3 | 0.5% | 100 | 70 | 23 | 5.3 | 1.2 | 30 |
| 4* | 0.5% | 150 | 90 | 9.0 | 1.0 | 0 | 10 |

*Benzoquinone was added to Sample 4.

Example 6

A purpose of this example was to illustrate a cross-linking strategy for cross-linking polysulfones produced according to various embodiments described herein. Commercially-available dicumyl peroxide (DCP) as illustrated in Structure F may be employed according to Reaction Scheme 5 to crosslink polysulfones produced according to various embodiments.

Structure F

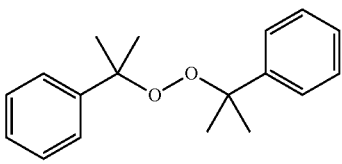

As shown in Reaction Scheme 5, adding DCP to a polysulfone according to various embodiments and applying heat may result in a crosslinked polymer network in which precise placement of the sulfone group is maintained.

Reaction Scheme 5

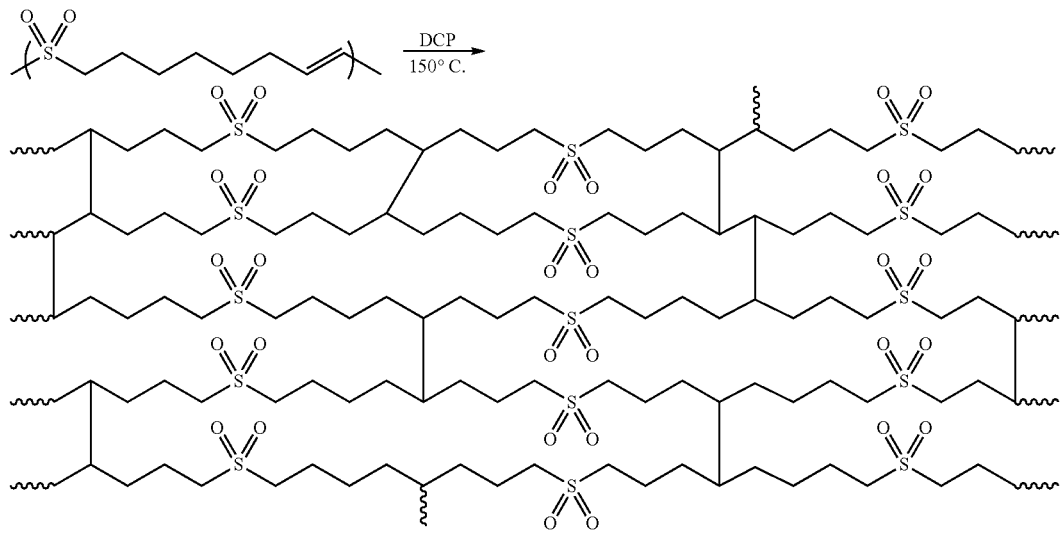

The characteristics of the crosslinked polymers indicate that the polymers may be particularly useful for durable materials.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

All patents, patent applications, provisional applications, and publications referred to or cited herein, supra or infra, are incorporated by reference in their entirety, including all figures and tables, to the extent they are not inconsistent with the explicit teachings of this specification.

It should be emphasized that the above-described embodiments of the present disclosure are merely possible examples of implementations and merely set forth for a clear understanding of the principles of this disclosure. It should be understood that the examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure and protected by the following claims.

What is claimed is:

1. A method for producing a polymer via metathesis polymerization, the method comprising:

forming a polymerization mixture, the polymerization mixture comprising a Ruthenium-based catalyst comprising a cyclic (alkyl) (amino) carbene ligand, having the structure:

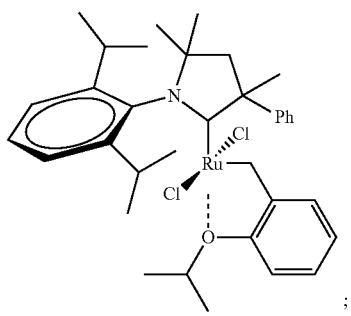

;

heating the polymerization mixture to a temperature greater than the melting point of the polymer in bulk conditions to form a molten polymerization mixture; and performing intensive mixing on the molten polymerization mixture to produce the polymer, wherein the polymer has a weight average molecular weight of at least about 10,000 Da within about 3 hours, and wherein the melting point of the polymer is 100° C. or greater.

2. The method according to claim 1, wherein the polymerization mixture further comprises one or more selected from
at least one cyclic monomer comprising an alkene,
at least one linear monomer comprising an α,ω-dieneyl-monomer,
and combinations thereof.

3. The method according to claim 2, wherein the at least one cyclic monomer or the at least one linear monomer comprises a functional group selected from alkyl, aryl, alkylaryl, ketone, aldehyde, ether, ester, carboxylic acid, alkylsilyl, arylsilyl, alkylarylsilyl, amine, epoxy, sulfone, sulfonic acid ester, and amides.

4. The method according to claim 1, wherein the metathesis polymerization is a metathesis ring-closure, and
wherein the polymerization mixture further comprises at least one acyclic non-conjugated diene.

5. The method of metathesis ring-closure according to claim 4, wherein the at least one acyclic non-conjugated diene comprises a functional group selected from alkyl, aryl, alkylaryl, ketone, aldehyde, ether, ester, carboxylic acid, alkylsilyl, arylsilyl, alkylarylsilyl, amine, epoxy, sulfone, sulfonic acid ester, and amides.

6. The method according to claim 1, wherein the metathesis polymerization is a metathesis olefin exchange, and
wherein the polymerization mixture further comprises at least one alkene.

7. The method of metathesis olefin exchange according to claim 6, wherein the at least one alkene comprises a functional group selected from alkyl, aryl, alkylaryl, ketone, aldehyde, ether, ester, carboxylic acid, alkylsilyl, arylsilyl, alkylarylsilyl, amine, epoxy, sulfone, sulfonic acid ester, and amides.

8. The method according to claim 1, wherein a degree of polymerization of from about 10 to about 100 is achieved in from about 3 to about 24 hours.

9. The method of metathesis polymerization according to claim 1, wherein the temperature is 120° C. or greater.

10. The method of metathesis polymerization according to claim 1, wherein the polymerization mixture further comprises a quinone.

11. The method of metathesis polymerization according to claim 10, wherein the quinone is benzoquinone.

* * * * *